US00PP36773P2

(12) United States Plant Patent
Hattori

(10) Patent No.: US PP36,773 P2
(45) Date of Patent: Jun. 24, 2025

(54) ***HELLEBORUS* PLANT NAMED 'BORUSMURA38'**

(50) Latin Name: ***Helleborus* x *sternii* (*Helleborus argutifolius* X *Helleborus lividus*)**
Varietal Denomination: Borusmura38

(71) Applicant: Miyoko Hattori, Tokyo (JP)

(72) Inventor: Miyoko Hattori, Tokyo (JP)

( * ) Notice: Subject to any disclaimer, the term of this patent is extended or adjusted under 35 U.S.C. 154(b) by 0 days.

(21) Appl. No.: 18/955,815

(22) Filed: Nov. 21, 2024

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

(56) References Cited

U.S. PATENT DOCUMENTS

PP21,003 P2 * 5/2010 Heuger ..... A01H 5/02
Plt./439

* cited by examiner

*Primary Examiner* — Karen M Redden
(74) *Attorney, Agent, or Firm* — C. Anne Whealy

(57) ABSTRACT

A new and distinct cultivar of *Helleborus* plant named 'Borusmura38', characterized by its relatively compact, upright to outwardly spreading and mounding plant habit; moderately vigorous growth habit; deeply serrated leaflets that have dark green-colored upper surfaces that are densely covered with lighter green-colored speckles and purplish red-colored marginal edges and lower surfaces that are light green in color; freely flowering habit; yellowish green-colored flowers; and good garden performance.

2 Drawing Sheets

Figure 1:
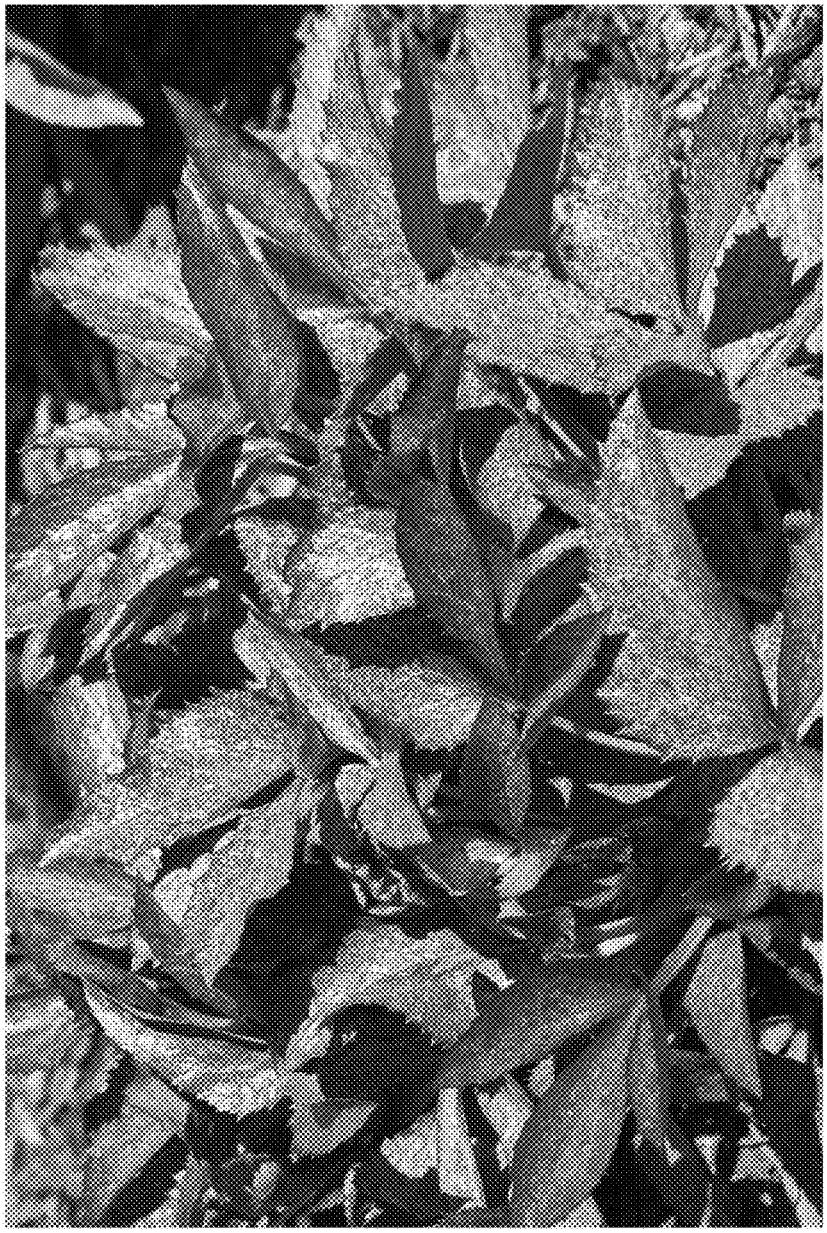

Botanical designation: *Helleborus* x *sternii* (*Helleborus argutifolius* X *Helleborus lividus*).
Cultivar denomination: 'BORUSMURA38'.

BACKGROUND OF THE INVENTION

The present invention relates to a new and distinct cultivar of *Helleborus* plant, botanically known as *Helleborus* x *sternii* (*Helleborus argutifolius* X *Helleborus lividus*), commonly referred to as an interspecific hybrid Hellebore and hereinafter referred to by the name 'Borusmura38'.

The new *Helleborus* plant is a product of a planned breeding program conducted by the Inventor in Kiyose, Japan. The objective of the breeding program was to create new uniformly mounding and freely-flowering *Helleborus* plants with attractive leaves and flowers.

The new *Helleborus* plant originated from a cross-pollination conducted by the Inventor in Toyko, Japan in March 2016 of an unidentified proprietary selection of *Helleborus argutifolius*, not patented, as the female, or seed, parent with an unidentified proprietary selection of *Helleborus lividus*, not patented, as the male, or pollen, parent. The new *Helleborus* plant was discovered and selected by the Inventor as a single flowering plant from within the progeny of the stated cross-pollination grown in a controlled greenhouse environment in Kiyose, Japan in March 2018.

Asexual reproduction of the new *Helleborus* plant by divisions in a controlled greenhouse environment in Kiyose, Japan since March 2018, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Borusmura38'. These characteristics in combination distinguish 'Borusmura38' as a new and distinct *Helleborus* plant:

1. Relatively compact, upright to outwardly spreading and mounding plant habit.
2. Moderately vigorous growth habit.
3. Deeply serrated leaflets that have dark green-colored upper surfaces that are densely covered with lighter green-colored speckles and purplish red-colored marginal edges and lower surfaces that are light green in color.
4. Freely flowering habit.
5. Yellowish green-colored flowers.
6. Good garden performance.

Plants of the new *Helleborus* differ primarily from plants of the female parent selection in the following characteristics:

1. Leaflets of plants of the new *Helleborus* have deeply serrated margins whereas leaflets of plants of the female parent selection have non-serrated margins.
2. Leaflets of plants of the new *Helleborus* are dark green in color and are densely covered with lighter green-colored speckles and purplish red-colored marginal edges whereas leaflets of plants of the female parent selection are solid greyish green in color.

Plants of the new *Helleborus* differ primarily from plants of the male parent selection in the following characteristics:

1. Leaflets of plants of the new *Helleborus* have deeply serrated margins whereas leaflets of plants of the male parent selection have shallowly serrated margins.
2. Leaflets of plants of the new *Helleborus* are dark green in color and are densely covered with lighter green-colored speckles and purplish red-colored marginal edges whereas leaflets of plants of the male parent selection are green in color flushed with white and without speckles.

Plants of the new *Helleborus* can be compared to plants of *Helleborus niger* X *Helleborus lividus* 'COSEH 700', disclosed in U.S. Plant Pat. No. 21,003. In side-by-side comparisons, plants of the new *Helleborus* differ from plants of 'COSEH 700' in the following characteristics:

1. Leaflets of plants of the new *Helleborus* have more deeply serrated margins than leaflets of plants of 'COSEH 700'.
2. Leaflets of plants of the new *Helleborus* are dark green in color and are densely covered with lighter green-colored speckles and purplish red-colored marginal edges whereas leaflets of plants of 'COSEH 700' are solid dark green in color and without speckles.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a close up view of a typical non-flowering plant of 'Borusmura38'.

Figure 2:
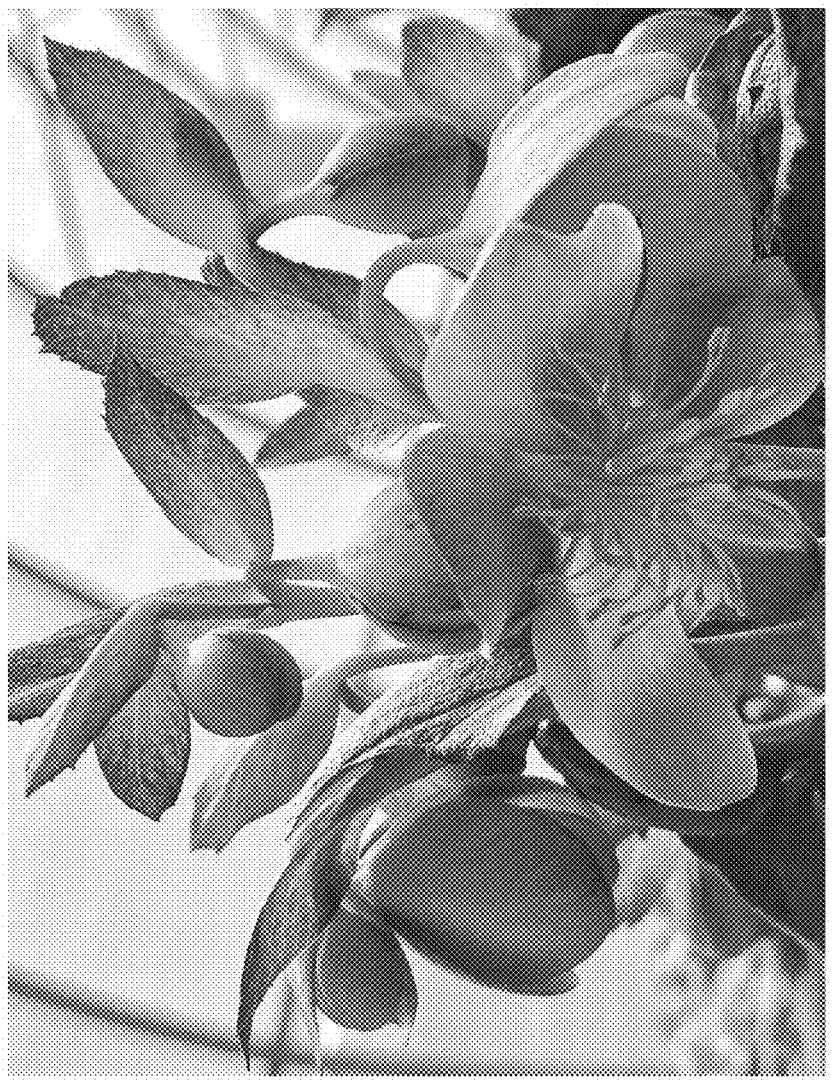

The photograph on the second sheet (FIG. 2) is a close-up view of a typical flowering plant of 'Borusmura38'.

DETAILED BOTANICAL DESCRIPTION

The aforementioned photographs and following observations, measurements and values describe plants grown during the late winter in an outdoor nursery in Smoketown, Pennsylvania and under cultural practices typical of commercial *Helleborus* production. During the production of the plants, day temperatures ranged from 17° C. to 22° C., night temperatures ranged from 5° C. to 10° C. and light levels ranged from 30 to 70 klux. Plants were 1.75 years old when the photographs and the description were taken. In the following description, color references are made to The Royal Horticultural Society Colour Chart, Sixth Edition, except where general terms of ordinary dictionary significance are used.

Botanical classification: *Helleborus* x *sternii* (*Helleborus argutifolius* X *Helleborus lividus*) 'Borusmura38'.

Parentage:

*Female, or seed, parent*.—Unidentified proprietary selection of *Helleborus argutifolius*, not patented.

*Male, or pollen, parent*.—Unidentified proprietary selection of *Helleborus lividus*, not patented.

Propagation:

*Type*.—By in vitro meristem culture.

*Time to initiate roots*.—About three to four weeks at soil temperatures about 20° C. and ambient temperatures about 22° C.

*Time to produce a rooted young plant*.—About six to eight weeks at soil temperatures about 20° C. and ambient temperatures about 22° C.

*Root description*.—Fleshy, medium in thickness; typically white to dark brown in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial; relatively compact, upright to outwardly spreading and mounding plant habit; overall plant shape, inverted triangle; moderately vigorous growth habit and moderate growth rate; leaves arranged in basal rosettes.

*Plant height, soil level to top of foliar plane*.—About 14 cm to 18 cm.

*Plant height, soil level to top of floral plane*.—About 14 cm to 18 cm.

*Plant diameter* (*area of spread*).—About 30 cm to 45 cm.

Leaf description:

*Arrangement*.—Leaves arranged alternately in a basal rosette; leaves palmately compound with typically three leaflets per leaf.

*Leaf length*.—About 12 cm to 15 cm.

*Leaf width*.—About 12 cm to 14 cm.

*Leaflet length*.—About 7 cm to 9 cm.

*Leaflet width*.—About 2 cm to 3 cm.

*Leaf shape*.—Compound trifoliate.

*Leaflet shape*.—Lanceolate to narrowly elliptic.

*Leaflet apex*.—Acute.

*Leaflet base*.—Center leaflet, attenuate; lateral leaflets, oblique.

*Leaflet margin*.—Deeply serrate.

*Leaflet texture and luster, upper and lower surfaces*.—Smooth, glabrous; leathery; matte.

*Leaflet venation pattern*.—Pinnate and reticulate.

*Leaflet color*.—Developing leaflets, upper surface: Close to 143A to 143B; speckles, close to 145C; marginal edges, close to 59B. Developing leaflets, lower surface: Close to 71A; proximally, tinged with close to 135D; at the apex, close to 71A. Fully expanded leaflets, upper surface: Close to 136A and 136B; dense speckles, close to 139C; marginal edges, close to 71A; venation, close to 138B. Fully expanded leaflets, lower surface: Close to 147C; marginal edges, close to 71A; midvein, close to 144D; lateral venation, close to 141B.

*Petioles*.—Length, fully expanded leaflets: About 7 cm to 9 cm. Diameter, fully expanded leaflets: About 3 mm to 5 mm. Strength: Strong. Texture and luster, upper and lower surfaces: Smooth, glabrous; matte and waxy. Color, upper surface: Close to between 144B and N144D. Color, lower surface: Close to 145B; proximally, speckled with close to 60B.

Flower description:

*Flower shape and habit*.—Single rotate cyanthiform flowers arranged in terminal and axillary cymes; freely flowering habit with typically about four to six flowers developing per cyme and about 120 to 160 flowers developing during the flowering season; flowers face outwardly to drooping.

*Fragrance*.—None detected.

*Natural flowering season*.—Plants flower continuously throughout February and March in Pennsylvania.

*Flower longevity on the plant*.—About three weeks; sepals are persistent and other flower parts are not persistent.

*Flower buds*.—Length: About 1.5 cm to 2 cm. Diameter: About 1 cm to 1.5 cm. Shape: Ovoid. Texture and luster: Smooth, glabrous; matte. Color: Close to 145B; at the marginal edges, tinged with close to 60B.

*Inflorescence height*.—About 14 cm to 16 cm.

*Inflorescence diameter*.—About 6 cm to 8 cm.

*Flower diameter*.—About 5 cm to 6 cm.

*Flower depth* (*height*).—About 2 cm to 3 cm.

*Petals*.—None observed; transformed into nectaries.

*Sepals*.—Quantity and arrangement: About four or five arranged in a single whorl. Length: About 2.5 cm to 3 cm. Width: About 1.5 cm to 2 cm. Shape: Oval. Apex: Obtuse. Base: Acute. Margin: Finely serrate. Texture and luster, upper and lower surfaces: Smooth, glabrous; matte. Color: When opening, upper surface: Close to 144D. When opening, lower surface: Close to 144D; at the apex, close to 71C. Fully opened, upper surface: Proximally, close to 144C and distally, close to 144D. Fully opened, lower surface: Close to 145C; venation, close to 141B.

*Peduncles*.—Length: About 2 cm to 3 cm. Diameter: About 2 mm by 4 mm. Strength: Moderately strong to strong. Aspect: About 15° to 20° from plant axis. Texture and luster: Smooth, glabrous; somewhat glossy. Color: Close to 145C to 145D.

*Reproductive organs*.—Stamens: Quantity per flower: About 30 to 50. Filament length: About 1.5 cm to 2 cm. Filament color: Close to 145D. Anther shape: Oblong and retuse; basifixed. Anther size: About 1 mm by 2 mm. Anther color: Close to 154B to 154C. Pollen amount: Scarce. Pollen color: Close to 1C. Pistils: Quantity per flower: About six to eight. Pistil length: About 1.5 cm to 2 cm. Stigma shape: Tapered, pointed. Stigma color: Close to 142B. Style length: About 1 cm to 1.2 cm. Style color: Close to 144D. Ovary color: Close to 144C.

*Nectaries*.—Quantity per flower: About six to eight. Length: About 6 mm to 8 mm. Width: About 1 mm to 2 mm. Shape: Tubular with circular apex. Margin: Entire; slightly undulate. Texture and luster, inner and outer surfaces: Smooth, glaucous; matte to slightly glossy. Color: When opening, inner surface: Close to 142B to 142C. When opening, outer surface: Close to 145C to 145D. Fully opened, inner surface: Close to 145A; towards the edges, close to 145D; with subsequent development, color becoming closer to 141D with marginal edges, close to N77B. Fully opened, outer surface: Close to 145B; towards the edges, close to 145D; with subsequent development, close to 142A to 142B with streaks, close to 142D with marginal edges, close to N77C to N77D.

*Seeds and fruits*.—To date, seed and fruit development have not been observed on plants of the new *Helleborus*.

Garden performance: Plants of the new *Helleborus* have been observed to have good garden performance and to tolerate rain, wind and temperatures ranging from about −15° C. to about 34° C.

Pathogen & pest resistance: To date, plants of the new *Helleborus* have not been observed to be resistant to pathogens and pests common to *Helleborus* plants.

It is claimed:

1. A new and distinct *Helleborus* plant named 'Borusmura38' as herein illustrated and described.

* * * * *